United States Patent [19]

Theurer

[11] Patent Number: 4,621,055
[45] Date of Patent: Nov. 4, 1986

[54] PROCESS FOR PRODUCING BIOLOGICALLY ACTIVE FACTORS

[76] Inventor: Karl Theurer, Brunnwiesenstrasse 23, 7302 Ostfildern 1 (Ruit), Fed. Rep. of Germany

[21] Appl. No.: 482,257

[22] Filed: Apr. 5, 1983

Related U.S. Application Data

[63] Continuation-in-part of Ser. No. 415,989, Sep. 8, 1982, abandoned, which is a continuation of Ser. No. 202,799, Jan. 3, 1980, abandoned.

[30] Foreign Application Priority Data

| Nov. 2, 1979 [DE] | Fed. Rep. of Germany | 2944277 |
| Nov. 2, 1979 [DE] | Fed. Rep. of Germany | 2944278 |
| Oct. 7, 1980 [EP] | European Pat. Off. | 80 106 066.6 |
| Oct. 31, 1980 [JP] | Japan | 55-152382 |

[51] Int. Cl.$^4$ ............................................. C12P 21/06
[52] U.S. Cl. ...................................... 435/69; 435/681
[58] Field of Search ................. 424/95, 195, 101, 103, 424/106; 435/68, 69

[56] References Cited

PUBLICATIONS

Lowe et al.—Affinity Chromatography (Pub. Wiley & Sons) 1974, pp. 6, 7 & 129–133.

*Primary Examiner*—Sam Rosen
*Attorney, Agent, or Firm*—Steele, Gould & Fried

[57] ABSTRACT

A process for producing biologically active factors from a substrate, in the form of cell homogenates of organ tissues, of microorganisms, plant components and/or body fluids. To this end, the substrate, in an aqueous form and freed of accompanying particulate substances, is selectively separated by affinity chromatography using a biological sorbent, in the case of which at least one nucleic acid (desoxyribonucleic and-/or ribonucleic acid) or at least one protein or peptide is coupled to a carrier substance; in the primary eluate components having no affinity are present, while the active factors (which have an affinity) are secondarily eluated. By binding nucleic acids or proteins from a given origin to a carrier, active factors with special properties such as tumor inhibiting substances, or stimulating substances may be positively produced.

4 Claims, 1 Drawing Figure

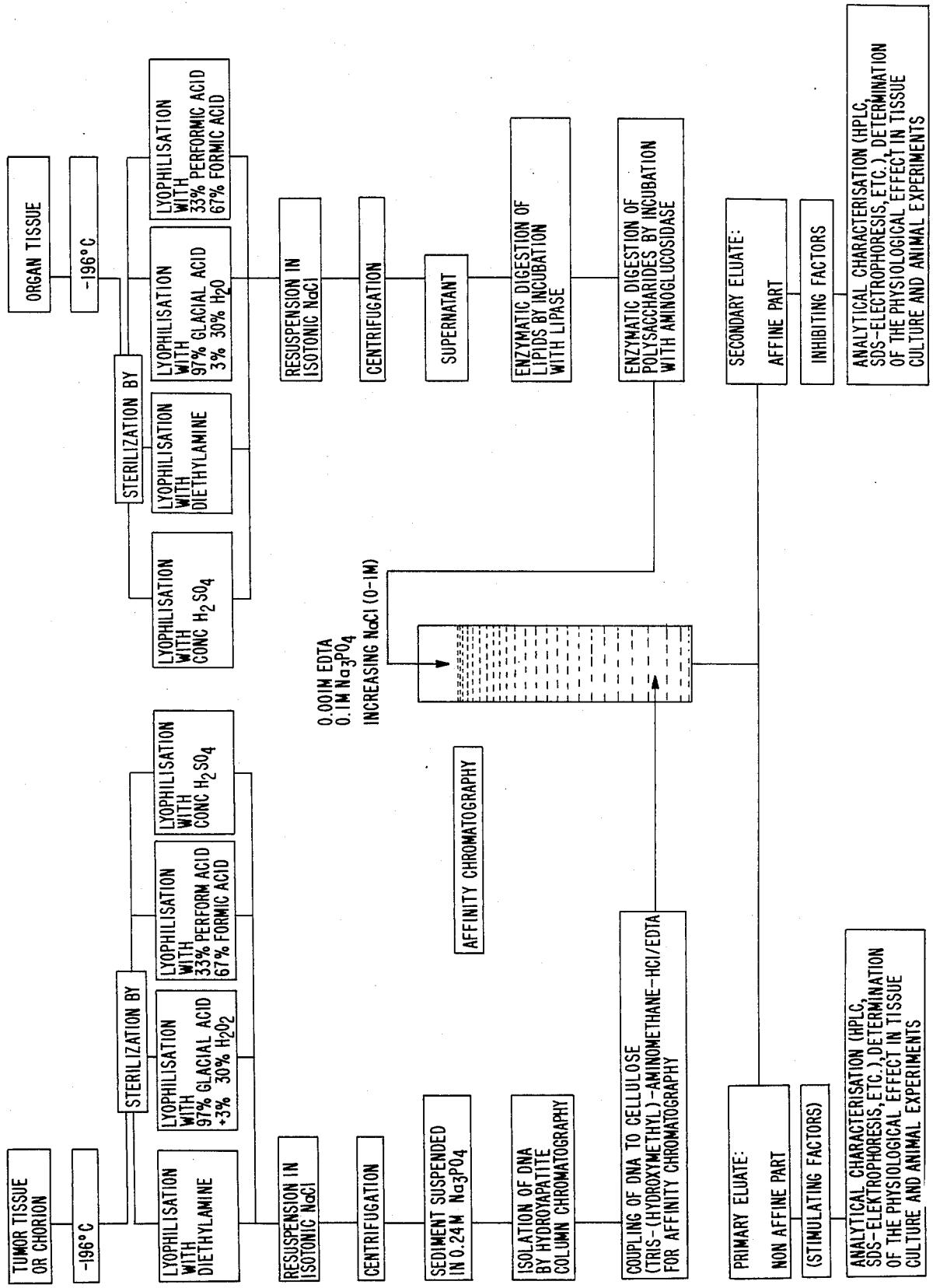

PROCESS FOR PRODUCING BIOLOGICALLY ACTIVE FACTORS

CROSS-REFERENCES TO RELATED APPLICATIONS

This application is a continuation-in-part of application Ser. No. 415,989, filed Sept. 8, 1982, now abandoned. Application Ser. No. 415,989, filed Sept. 8, 1982 is a continuation of application Ser. No. 202,799, filed Jan. 3, 1980, now abandoned.

BACKGROUND OF THE INVENTION

The present invention relates to a process for producing biologically active factors from a substrate in the form of cell homogenates of organ tissues, of microorganisms, of plant material and/or of body liquids. More specifically, the invention is directed to obtaining sterile, biologically active factors which may be used for the stimulation and, on the other hand, for the inhibition of processes of growth, metabolism, and of synthesis in eukaryotic and prokaryotic cells and tissues.

On the basis of data from my own experiments with respect to effects on growth and metabolism of human tissue cells in cell cultures by treatment with macromolecular organ extracts (V. Paffenholz and K. Theurer: Einfluss von makromolekularen Organsubstanzen auf menschliche Zeller in vitro, I. Diploide Kulturen, II. Tumorzellkulturen (the effects of macromolecular organ substances on human cells in vitro, I. diploid cultures, II. tumor cell cultures): Der Kassenarzt, no. 27, pages 5218 to 5226, 1978, no. 19, pages 1876 to 1887, 1979), it has been seen than an inhibitory effect on tumor cells and heteroploid cells was produced at high dilutions in a concentration of $10^{-6}$ to $10^{-9}$ g/ml of culture medium, and stimulation of healthy normal cells was produced using high concentrations between $10^{-3}$ to $10^{-6}$ g/ml of culture medium. The active factors were identified as proteins and peptides.

In view of these differences, it seemed likely that different factors were effective for inhibition and stimulation with different sites of action (K. Theurer: Prophylaxe und Therapie von Praekanzerosen und Malignomen mit makromolekularen Organextrakten (prophylaxis and therapy of precanceroses and malignant tumors with macromolecular organ extracts): Krebsgeschehen 4, pages 80 to 86, 1980). This was responsible for the development of the present process for separating inhibiting and stimulating factors from cell homogenisates. Studies of S. R. Burzynsky, Z. Stolzmann, B. Szopa, E. Stolzmann and O. P. Kaltenberg (Antineoplaston A in Cancer Therapy: Physiological Chemistry and Physics, 9, pages 485 to 500 (1977)), make it clear that such tumor inhibiting factors are present in the urine of healthy individuals and may be produced therefrom. It is furthermore known that tumor inhibiting factors are present in the blood of healthy individuals.

One purpose of the invention is that of producing active factors from biological substrates selectively and freeing them of undesired accompanying substances so that they may be used for scientific and therapeutic purposes and in industry.

In the present invention the substrate, in an aqeuous form, and free or freed of accompanying particulate substances is selectively separated using a biological affinity sorbent, in which at least one nucleic acid, or at least one protein or peptide, is coupled with a carrier substance. Non-binding components are contained in the primary eluate and the active factors, having an affinity, are secondarily eluated. In this respect, the wording "primary eluate" is used in the sense of an eluate which is provided by simple rinsing of the sorbent, while on the other hand, for producing or obtaining the eluate with the binding active substances in it, special adjuvants are used having the effect of desorbing the active substances or factors from the affinity sorbent. In this respect not only the primary, but furthermore the secondary eluate may undergo further fractionation, in which respect, in the case of the secondary eluate, physico-chemical fractionating operations are preferred.

With the selective biological separating process of the invention for active substances or factors it becomes possible for biologically active substances or factors having given properties to be separated positively on a substrate made up of a great number of different materials. Separation of the substrate into components is preferably undertaken by affinity chromatography or by a combination of affinity chromatography and electrophoresis. The electrophoresis may be undertaken in the form of "Free-flow-Electrophoresis". The affinity chromatography makes possible selective separation into or of desired active factors, in which respect the nucleic acids or the proteins, which are coupled with the carrier substance for forming the affinity sorbent, are selected in a way dependent on the desired properties of the desired active factor or factors. The nucleic acids, or, in the other case, the proteins or peptides, used for producing the affinity sorbent, are, for their part, preferably isolated from a substrate of the sort noted at the start. More specifically, if the nucleic acids, or in the other case, the proteins or peptides for the affinity sorbent, are to be isolated from such a substrate, it is best for the substrate to be freed, before separating off these substances, of undesired or ineffective accompanying substances. The undesired or ineffective accompanying substances may be enzymatically degraded, whereafter the products of degradation may be removed by dialysis of fragments or by ultrafiltration. In this respect, as a general rule, products with a molecular weight under 600 will be removed, because it has turned out that the biologically interesting active factors have a higher molecular weight, and, more specially one of the order of 600 to 1,000,000. The enzymatic degradation is preferably undertaken positively in a way dependent on the sort of desired active substances. Carbohydrates and lipids may, generally speaking, be removed, while on the other hand, proteins or nucleic acids will only be removed if they are undesired as active substances. If only polypeptides or proteins are desired as the active substances, this generally being the case, the nucleic acids may be degraded as well. If, the other way round, the desired active substances are nucleic acids, for example for further use as affinity sorbents, it is then possible for the polypeptides or proteins to be degraded. Desoxyribonucleic acid will most often be the preferred nucleic acid because, from the biological point of view, it is more interesting. For special purposes, however, ribonucleic acid may be used.

Before separating, and more specifically, before the removal of any undesired accompanying substances, the substrate is best sterilized. If a material change in the biological substances is not of key importance, conventional ways of sterilizing, as for example chemical sterilization or sterilization with ionizing radiation may be utilized. More importantly, however, sterilization by condensing volatile substances with sterilizing properties onto the substrate, in the form of a powder, is to be preferred, as the preferred starting material is also in the form of a powder; the substances for this purpose which are more specially preferred are those in the case of which any excess may be removed by evaporation or sublimation. Sterilization is best undertaken in vacuo using pressure variations.

The affinity sorbent may be produced by coupling highly purified nucleic acid fractions or protein (or, in the other case) peptide fractions to inert carrier substance for affinity chromatography of the substrate. The discovery has been made that carrier-bound protein or peptide fractions have a specially high degree of avidity for stimulating acting substances and carrier-bound nucleic acid fractions have such an avidity for inhibitory active substances, for which reason they are preferred for use on these lines for producing the active substances in question in the secondary eluate. In this respect, it is furthermore important from which biological material the protein or peptide fractions on the one hand, and the nucleic acid fractions on the other hand, are produced, which are used for producing the affinity sorbent, as explained in more detail hereinafter. By making the right selection, it is, for this reason, possible to make certain that given active factors, present in the substrate and having given properties, may be positively separated out.

The invention is directed not only to the process for producing or obtaining the active factors, but is furthermore directed to the active factors per se, which may be obtained with the process of the invention, and furthermore to the use of such substances. Detailed working examples will be given herein of the invention. In this respect, it is to be noted that the substrate may be produced from any sort of biological material containing active factors. The most important of such starting materials seem to be body fluids such as blood, cerebrospinal fluid, amnion-exudates, transsudates, and fluids expressed from tissues and urine.

In a preferred form, the process of the invention may be divided into a number of preferred steps, which may be combined together in any suitable way, namely:

(a) non-destructively sterilizing the starting materials to eliminate any viral components, while, at the same time, increasing the quality of the hydrophilic properties, that is, the water solubility by partial lysis of the molecular sub-units and the addition of radicals of the acids and alkalis used, (b) separating (first-stage) ineffective or otherwise undesired components of the substrate, (c) coupling of highly purified desoxyribonucleic acid and/or RNA fractions, more specially, ribosomal RNA and, on the other hand, of protein and peptide fractions to activated inert carrier substance for forming the affinity sorbent for affinity chromatography of the substrate to be separated into its components, (d) separating (second-stage) the substrate, produced in step (b), on the affinity sorbent, prepared in step (c), by sample inlet and elution steps, (e) obtaining tumor-inhibiting factors by affinity chromatography of substrates produced from fetal and/or juvenile normal tissue and/or body liquids of healthy individuals on carrier-bound DNA, (f) producing stimulating factors, (g) producing organ-specific fractions, and (h) producing fractions from micro-organisms and plant cells.

The intermediates of process steps (a) may be used per se. The sort of use and further processing of the products made in this process will be given in further detail hereinafter. On the other hand, steps (a) and (b) are not necessary for processing the substrate. A particularly interesting aspect of the invention is, however, the sort of sterilization and first-stage treatment of the substrate to be separated and electrophoretic elution of the proteins, adsorbed on the carrier-bound substances, by changing the voltage or current level and furthermore the use of special starting materials and their application. Scientific details and the sort of the application and further processing are in line with the present stage of development of the art.

A condition for therapeutic use of active substances from biological tissues in sterility with respect to viruses. Government prohibition of processing medicaments with ionizing radiation and of denaturizing by chemical processing makes a specially non-destructive sterilization step (a) of key importance. This process step is furthermore beneficial with respect to undertaking further process steps later because, at the same time, there are better hydrophilic properties and the partial cleavage into molecular sub-units is effected. The acidic or alkaline effect produced by addition of acids and alkalis may readily be neutralized by the right form of buffering so as to make certain of the best pH-value in the separating operation.

In the case of cell cultures and animal experiments a significantly better inhibitory effect on tumors and a stimulating effect in the case of normal tissue was produced by preparations obtained using process step (a) than is the case with preparations which only underwent freeze-drying. For this reason, it seems clear that process step (a) has a favorable effect on the efficacy of the end-product.

In process step (a) use is preferably made of vapors of concentrated acids or alkalis, and, more specially, concentrated sulfuric acid, acetic acid, formic acid or diethylamine and/or mixtures or peracids with the corresponding concentrated acids, the pulverized substrates or concentrates being acted upon by the vapor of the substance, which is to have an effect on them, in vacuo at room temperature without any further heating, the vapor condensing on the substrate. In German Pat. No. 1,090,821, whose process details may be used in the present invention, the workings of such a process are noted in connection with a partial breaking up of the starting material. The discovery has now been made that on using materials with sterilizing properties, this process gives very high-level effects, per-compounds being more specially preferred in this connection.

Obtaining or producing sterile medicaments from biological tissues, more specially organ tissues, is frequently hard to undertake because, using conventional disinfectants, full sterility may not be produced without great denaturization and loss of the therapeutic efficacy. For this reason, public health authorities have enacted specially tight rules for producing such medicaments, as for example the keeping of isolated groups of animals and breeding them under sterile conditions. Because of such rules or conditions, there has been an overly great increase in price of the products without, however, producing any full and complete warranty for sterility, more specially with respect to viruses. On the other hand, the use as well of antibiotics and/or chemotherapeutic agents having the property of inactivating viruses, is linked with the risk of making the patient allergic.

In experiments with organ powders produced fro virus-infected chicken embryos, it has been possible to make clear that sterility may be produced by a modification of the process for the controlled chemical breaking up of organs for therapeutic purposes (see German Pat. No. 1,090,821). The process is modified in that the substrates, with 5% to 30% of residual water (in comparison with a normal level of 60% to 87% of water in fresh tissues) are acted upon by the vapors of acids in vacuo, there being the addition, to these acid vapors, of the corresponding peracids, more specially of formic acid, acetic acid or sulfuric acid, in a mixing ratio of 1 part of peracid to 1 to 4 parts of the corresponding acid anhydride. Furthermore, vapors of acids may be used, to which, on producing them, a smaller amount of hydrogen peroxide is added than will be necessary for producing the peracid itself, for example there would be the addition to 10 parts of 98% formic acid of 0.1% to 0.8% of 30% hydrogen peroxide together with 0.5% of concentrated sulfuric acid in place of 10 parts of concentrated formic acid with 1 part of hydrogen peroxide, and in the case of 10 parts of acetic anhydride there would be the addition of only 0.5 to 4 parts of fresh 30% hydrogen peroxide (in place of 5 parts of the same). The useful effect of this process is that the "partial" peracids are less aggressive and may be more readily handled, that is to say with less danger of explosion.

On causing the substrate to be acted upon by vapor, the amount of acid, which becomes condensed on the substrate, is best so controlled that in effect it is equal to a 0.5% to 2% peracid. The condensation operation may, if necessary, be undertaken a number of times by stepping down the vacuum level for a short time before the acid vapors are run into the apparatus again for condensing on the substrate. If the amount of acid is not metered, the sterilization operation may be undertaken for some minutes, whereas if the amounts of acid are limited or measured out for a given amount of substrate, the operation may be undertaken for a number of hours.

The test for sterility of the substrate may be undertaken by ways which are conventional in microbiology and virology by culturing the viruses in hen's eggs or in cell cultures. The testing or assaying of the biological activity of the preparations still in existence is undertaken by bioassay using cell cultures (see V. Paffenholz and K. Theurer: Einfluss von makromolekularen Organsubstanzen auf menschliche Zellen in vitro (The effects of macromolecular organ substances on human cells in vitro), supra) and by animal experiments.

The process is not responsible for any products with a toxic effect, as for example heterocyclic compounds, because the fragments produced do not (because of the absence of water) undergo reaction or conjugation with each other. The peroxides produced at a low level are responsible, on therapeutic application, for a desired stimulating effect in the substrates like that of ozone when therapeutically used. Furthermore, in the case of this process, the acid which has so far not undergone reaction, may be drawn off by stepping up the vacuum.

In other respects, however, it is furthermore possible for neutralization to be caused by blowing in alkali vapors as for example of mercaptoethanol and then drawing off again. By the simultaneous reducing effect, the oxidation effect may, in part, be cancelled out again.

The use of peracid vapors makes necessary the use of acid-resistant plastic piping and glands. The vessel for the peracids may best be connected by means of a three-way cock with the vacuum pump and, or the other hand, with the recipient for the substrate so that, after producing the vacuum in the substrate recipient, the vacuum pump may be cut off and the acid vapors run into the apparatus.

It is furthermore possible for frozen, undried tissue powder to undergo drying before hand (by freeze-drying to get down to the desired residual moisture level, or by drying in the presence of hygroscopic materials such as concentrated sulfuric acid) before the sterilization operation is started. If the residual moisture level in the dried tissues is overly low, they may be processed in a first stage by running water vapor into the apparatus, or by moistening directly.

Details in connection with peracetic acid for "cold sterilization" for thermosensitive instruments have been given in a paper by K. Bansemir, H. Bellinger, K. Disch and W. Kastner in "Hygiene und Medizin" 4 (1979), pages 311 to 316, from which it will be seen that sterilizing effects are produced with a 1% to 2% solution in the case of papova-viruses, Entero-viruses, Poliomyelites type I and furthermore in the case of Coxsackie viruses type B III and Hepatitis-B viruses. An account was furthermore given on toxicological testing. The use of acid solutions as such is, however, not the same as the process of the present invention, because in it the operation takes place at room temperature and with the application in the form of acid vapors, and furthermore on the drying operation the acid, which has not undergone reaction, is drawn off again.

The acid vapor lysis process in vacuo (a) is used as such furthermore for controlled chemical digestion of organs for therapeutic purposes and more specially of fetal, embryonic juvenile tissues, of fetal bovine liver, thymus, spleen, cardiac muscle and brain for producing special preparations for the treatment of neoplasms and diseases of the immune system.

The sort of digestion and degradation of biological tissues is of key importance for their therapeutic effect, as has been seen to be the case for fetal and embryonic organ preparations produced by the process for controlled chemical digestion of organs and for therapeutic purposes (German Pat. No. 1,090,821). The use of such preparations, more specially, of fetal liver, spleen, thymus, cardiac muscle and brain has not been responsible for any incompatibility in the case of animal experiments or in the case of use on humans. The effect of preparations made from fetal and young bovine liver has been surprising in oncology. Although the relation between the carcino-embryonic antigen (CEA) and tumor antigen is known, no report has been come across in the literature to the effect that good prophylactic and therapeutic effects may be produced in the case of experimental tumors by using liver preparations. This has, however, turned out to be the case with preparations produced by the present process in testing on a methylcholanthren induced tumor (which was induced some years back in the Sloan Kettering Institute of Cancer Research in New York) on transfer by innoculation to mice.

Furthermore, in animal experiments, it was possible for antibody formation to be forced down to a lower level on using preparations of fetal bovine thymus and fetal spleen. This biological immune suppression is important for the treatment of allergic diseases and has furthermore been seen to take place in the case of man on the therapeutic application of such preparations.

On the other hand, in animal experiments using the hemolysis plaque test, as illustrated in Examples 6 and 7, it was possible to determine that such preparations from fetal cardiac muscle, fetal liver and brain make possible an even more intense stimulation of antibody synthesis than is the case with conventional immune stimulants.

The hemolysis plaque technique makes it possible to get readings for the level of immunological defense from the number of influenced antibody-forming cells in the spleen. If there is a greater plaque formation than in the untreated control, this is a sign for a stepping up of immune defense while, on the other hand, a lower figure for plaque formation indicates a drop in immune response. To this end, mice were sensitized with respect to washed ovine erythrocytes and additionally pre-treated with preparations (produced by the claimed process) from fetal organs, used in an aqueous, diluted form, and then, at different times later on after the injection, the mice were splenectomized. Then a spleen cell suspension was made up, which, together with the ovine erythrocytes and agarose were poured into petri dishes as a thin layer. After incubation for one hour, the development of the plaque-forming cells took place with diluted guinea pig complement, which is necessary for the lysis of the cells in addition. The control group was made up of mice which had not had any organ preparations.

The dry organ powders produced by the present process from fetal and juvenile tissues were taken up directly in physiological sodium chloride and suspended or dilutions in water thereof were prepared. Not only the suspensions, but furthermore the diluted solutions may be injected parenterally.

The process step (b) for the preliminary separating off of ineffective components from the substrate which is to be processed is, on the one hand, for conditioning the affinity sorbent and, on the other hand, for pre-processing the substrate which is to be separated. For this reason, these two preliminary separating operations may be undertaken separately. On the other hand, for separating operation (d) it is possible to make use as well of substrates which have not undergone the part-processes (a) and (b), or have only undergone them in part and which are of different origins. Furthermore, mixtures of different starting materials may be used, although, however, it is best for the ineffective components of the substrate as for example polysaccharides, glycogen, lipids and possible ribonucleic acid (RNA) to be removed conventionally, this furthermore being true for the DNA from the substrate to be separated, if such DNA is not the desired active factor.

The separation off of ineffective or undesired components is not necessary in the case of the substrate to be separated, because the desired active factor is, as we have seen, selectively bound by the affinity sorbent. Only the nucleic acid components (DNA and/or RNA) of the starting substrate or only the protein or peptide fractions of the same are needed for readying the apparatus used for affinity chromatography. For separating, fractional centrifugation of the cell and tissue homogenisates (or suspensions from the dry powder) is used giving a 100,000 g supernatant top layer (see V. Allfrey: Isolation of subcellular components: The Cell: Vol. I, I. Brachet and A. E. Mirsky, Editors, Academic Press, London, 1959—National Cancer Institute Monograph 21: Development of Zonal Centrifuges and Auxillary Systems for Tissue Fractionation and Analysis: National Cancer Institute Bethesda, Md., USA, 1966).

For further isolation, the single fractions of cell nucleic mitochondria, ribosomes and the supernatant top layer are processed with enzymes: for example with ptyalin and maltase and with beta or gamma amylase for the degradation of saccharides, with amyloglucosidase for the degradation of glycogen, with lipase for the degradation of lipids, with RNases for the degradation of ribonucleic acids, with DNase for the degradation of DNA and with proteinases or peptidases (as for example pepsin, papain, trypsin) for the degradation of proteins and peptides. As will be clear, in the preliminary separation of the peptide fractions, no proteinases or peptidases are used and, on producing the nucleic acid fractions, no nucleases are used. (For papers on the isolation of DNA from cells, see: W. Meinke, D. A. Goldstein, M. R. Hall; Anal. Biochem, 58, 82 (1974); G. G. Markov, I. G. Ivanov: Anal. Biochem, 59, 555 (1974); I. G. Ivanov, P. Venkov, G. G. Markov: Preparative Biochem., 5, 219 (1975)).

The degradation products produced by the enzymatic cleaning step may furthermore be removed by dialysis or ultrafiltration to less than 600 molecular weight (see B. L. Williams and K. Wilson: Praktische Biochemie—Grundlagen and Techniken, page 106: publisher: Georg Thieme Verlag, Stuttgart, (1978)). On isolation the ionic environment and the pH of the substrate may only be changed to such a degree that no denaturing of the active substances takes place.

For getting ready for the separation by affinity chromatography in working step (c), the nucleic acid fraction (mostly DNA) or, however, the protein or peptide fraction is coupled to inert carrier material, as far as possible by covalent bonds, to functional chemical groups, without this being responsible for the blocking of reactive bonding sites having a specific effect. A carrier material may, for example, be cellulose, Sephadex hydroxylapatite, polyacryloamide gel, granulated polyethylene, agarose, glass beads, silicone particles, silica gel, zinc oxide, aluminum hydroxide etc. Furthermore, detailed forms of the processes are known in the art (see E. Paoletti et al.: J. Biol. Chem. 249, 3273 (1974)N. Signal et al.: Proc. Nat. Acad. Sci., USA 69, 3537 (1972); R. L. Tsai, H. Green: J. Mol. Biol., 73, 307 (1973); Sutton, D. and Kemp. J. D.: Biochemistry 15, page 3153 (1976); Smith, I. et al.: Anal. Biochem., 48, page 27 (1972); I. A. Lautenberger, S. Linn: J. Biol. Chem. 247, 6176 (1972); and on the question of binding of proteins or peptides to carrier substances see: G. F. B. Schumacher and W. B. Schill: Anal. Biochem. 48, 9 (1972); E. D. Sevier: Anal. Biochem. 74, 592 (1976)). The carrier-bound nucleic acid or protein fraction is now used as a column filling for affinity chromatography (see P. Cuatrecasas: Affinity Chromatography of Macromolecules: Advances in Enzymology. Ed. by A. Meister: 36: 29, 1972. Interscience, New York; F. Friedberg, Chromatography Reviews 14: 121, 1971).

In this respect, a preparative chromatographic column or a combined apparatus for chromatography and electrophoresis on the lines of Free-Flow Electrophoresis may be used (see N. Seiler, I. Thobe, G. Wetner: Elektrophorese im traegerfreien Pufferstrom (electrophoresis in a carrier-free buffer current): Z. Physiol. Chem. 351, 865 (1970); K. Hannig: Z. Anal. Chem. 338, 211 (1964)). The use of carrier-bound filler in the case of this free-flow electrophoresis has so far not been noted in the literature.

The recovery of stimulating fractions from the substrate is undertaken in a separating apparatus with a carrier-bound protein fraction, while the separation of the inhibiting factors takes place in an apparatus with DNA fractions, in the secondary eluate. As soon as the packing of carrier-bound fraction is saturated by absorption of substrate to be separated, the apparatus is rinsed thoroughly with a buffer solution of low ionic strength. This secondary elution takes place of the absorbed fraction. This elution may be undertaken by increasing the ionic strength and changing the pH value of the buffer used. A new process which is specially useful and is very free of undesired effects, makes use of an AC field at a suitable frequency. This sort of elution has so far not been noted in the literature. The useful effect is that the apparatus may be used again, after thorough rinsing with the buffer solution used for primary desorbing. Furthermore, this purpose is furthered by the effect of an electromagnetic field which is normal to the direction of motion of the buffer solution, possibly in combination with electrophoresis. The separation of the substrate in the separating apparatus, readied in process step (c), is best undertaken by sequential or on-off inlet of sample and elution steps. In this respect, in a first step, the components without affinity are produced and then, after cleaning the apparatus by rinsing as a secondary step, elution of the absorbed active factor takes place as detailed earlier. The primary eluate and the secondary eluate have the opposite effective components in them.

For producing tumor-inhibiting factors (e), the separating apparatus is best conditioned with carrier-bound DNA from fetal tissues and/or from different tumor tissues. The absorbing factor may, for this reason, be made up of a single starting substance or of a combination of different substances as for example different sorts of tumors and metastases, such as solid tumors and leukemic cells, which are produced in cell cultures, possibly combined with fetal tissues.

The genus or organ specific factors of the substrates to be separated may be produced or obtained by using carrier-bound factors, which are different for the substrate to be separated. The separating operation takes place using the proteins in question with special degrees of specificity as absorption materials. For this reason, for example, factors, which are contained in the liver, may be isolated from kidney tissue or from an other tissue; on the same lines it is furthermore possible for feto-embryonic and carcino-embryonic antigens and components to be produced from body fluids.

This process is furthermore used for producing inhibiting and stimulating substances with respect to microorganisms. In this respect, carrier-bound DNA from micro-organisms is used for separating the substrate of the parallel extracts from like or different micro-organisms. In this way it is possible for natural biological antibiotics to be produced while on the other hand stimulating factors take effect on the reproduction and effect of micro-organisms with special functions, as for example of micro-organisms, modified by gene transfer for the synthesis of biological factors as for example insulin and interferon. On these lines, the desired effect of oleophagic micro-organisms may be activated. In the same sort of way, plant factors may be separated, possibly for producing biological plant protection substances or growth factors. On the other hand, the process may furthermore be used for isolating certain gene sections. In this respect, the protein fraction, which has been isolated and identified beforehand, is used in a carrier-bound form for separating off the DNA fraction in question. The DNA gene sections to be isolated will then be in the secondary eluate.

Taking a general view, it may be seen that the present invention is more particularly directed to producing, that is to say obtaining, sterile biological active factors for stimulating, and on the other hand for inhibiting, events in connection with growth, metabolism, synthesis in eukaryoic and furthermore prokaryoic cells and tissues, from cell homogenisates produced from organ tissues, micro-organisms, plant components and/or body fluids (blood, cerebrospinal fluid, amnion-exudates, transsudates, fluids expressed from tissues and urine). A list and further details will now be given to preferred forms of the working steps detailed so far:

(a) the sterilization, with as little undesired effect as possible, of biologically active substances, more specially with respect to viral components and producing better hydrophilic properties, the partial cleavage into molecular sub-units and the addition of radicals from acids and alkalis or bases (used in vapor form), and more specially of concentrated sulfuric acid, acetic acid, formic acid or diethylamine and/or mixtures of peracids with the parallel concentrated acids, in which respect the pulverized substrates or concentrates with the agent for producing the desired effect (and whose boiling point at atmospheric pressure is greater than room temperature) put together in a shut-off or sealed system, but without mixing, are acted upon by such a vacuum as makes possible a change of the agent (for producing the desired effect) into the vapor phase; and, after the desired effect has been produced on the substrate, the unreacted agent is removed again, the starting materials more specially being frozen and pulverized organic tissues, and the chemical agent in vapor form from a preset amount is condensed firstly onto the substrate by lowering the vacuum and, after the desired effect has been produced, the excess agent is removed against by increasing the vacuum and the products so processed are used per se or in the further process steps;

(b) the preliminary removal of ineffective components from the substrate (containing, for example, polysaccharides, lipids, ribonucleic acids and desoxyribonucleic acids (DNA) or, however, protein or peptide fractions) takes place by centrifuging off the cell nuclei and cytoplasmatic components and/or enzymatic degradation, for example using ptyalin and maltase, lipases, RNases, DNases, proteinases or peptidases, dialysis of fragments under a molecular weight of 600 or ultrafiltration;

(c) the coupling of highly purified desoxyribonucleic acid fractions or, on the other hand, of protein or peptide fractions to activated inert carrier material for affinity chromatography of substrates as produced in step (b), in which respect for producing stimulating factors, carrier-bound protein or peptide fractions (or in the case of producing inhibiting factors, carrier-bound DNA fractions) are used for getting ready a preparative chromatographic column or a combined chromatographic and electrophoresis apparatus on the lines of free-flow electrophoresis, if desired, with electrophoretic elution by changing the voltage or current level;

(d) separating the substrate produced in step (b) in separating apparatus as made ready in step (c), by sample input and elution steps, in which respect, in a first working step the component having no affinity is produced and in a further cleaning rinsing operation undertaken on the apparatus, the elution of the absorbing active factor is undertaken by using an electric DC field or an AC field of the necessary frequency and/or of an electromagnetic-field or by changing the buffer solution;

(e) producing tumor-inhibiting factors by affinity chromatography of substrates, from fetal and juvenile normal tissues and/or body fluids from healthy individuals, or carrier-bound desoxyribonucleic acid from fetal tissues and/or from different tumor tissues or from tumor cell lines cultivated in vitro by themselves or in combination by secondary elution of carrier-bound fractions (whereas the stimulating factors are produced by undergoing primary elution);

(f) producing stimulating factors as well from substrates produced from normal tissues and/or body fluids of healthy individuals by affinity chromatography on carrier-bound protein or peptide fractions from healthy tissues by a second elution operation, while the inhibiting fractions are in the first eluate;

(g) producing organ specific and/or fetal components using, on the same general lines, the DNA, RNA, or protein (or peptide) fractions of the parallel organ tissue, more specially from fetal, embryonic and/or juvenile tissues of healthy individuals, as for example liver, thymus, spleen, cardiac muscle, brain etc.; and (h) producing inhibiting or stimulating substances for micro-organisms or plants from the parallel extracts making use of carrier-bound nucleic acids.

The isolated factors may be used in aqueous solutions or incorporated in liposomes or in a water-in-oil emulsion (see German Pat. Nos. 2,650,502, 2,656,333 and 2,640,707) in an aqueous phase and, on the other hand, after further separating and cleaning their structures may be elucidated and partly or completely synthesized, this being a further part of the present invention. The isolated, inhibiting proteins or peptides may furthermore be effective for the isolation of certain desoxyribonucleic acids (which may be used as gene sections) in a carrier-bound form for affinity-chromatographic separation of such DNA mixtures or solutions, the DNA sections, which are to be enriched or isolated, being present in the secondary eluate.

An account will now be given of further measures and useful effects of the invention using preferred working examples.

EXAMPLE 1

Breaking up and sterilization of dry powder produced from liver, using sulfuric acid in vacuo One hundred (100) g of finely pulverized dry liver powder are spread out on to a petri dish in the form of a 0.5 cm high layer and placed in a desiccator, which may be joined up as desired with a cold trap by way of a high-vacuum pump system or, at the same time, with a communicating vacuum vessel as well, which may be shut off from the main desiccator by a valve.

Firstly, concentrated sulfuric acid at room temperature is placed in the communicating vacuum vessel and the connection with the desiccator is shut off. For clearing of any residual moisture caused by the hygroscopic effect of the dry powder, firstly, with the help of the cold trap (which is supercooled with acetone and carbon dioxide snow), water is sublimed from the tissue powder and then, shutting off this condenser, with the help of the high-vacuum system exhaustion is taken down to a pressure in the desiccator of $10^{-4}$ torr. Thereupon the valve to the communicating vessel is opened so that it is now possible for the sulfuric acid, in the form of vapor, to go into the desiccator.

The vacuum will now go down to vapor pressure of the sulfuric acid. The connection to the acid vessel is now shut off, but not, however, before separating the communicating vessel from the pump system. By blowing nitrogen into the desiccator, the vacuum over the liver powder is only decreased further to a very small degree. For this reason, sulfuric acid vapor will be condensed onto the liver powder. After a certain time for it to take effect, the connection with the pump system and with the communicating vessel is opened again for the acid and after getting to the vapor pressure of the sulfuric acid, the operation is performed two further times. Lastly, the connection between the two communicating vessels is not opened again and in fact only the connection between the desiccator and the pump system is opened. Pumping is now undertaken for exhaustion until all the sulfuric acid has been cleared from the desiccator which has not chemically reacted. In this way, it is possible, furthermore, for the hydrogen ion concentration in the dry powder produced from liver to be put at any desired acid level. The longer and stronger the exhaustion operation, the more neutral will be the pH value.

EXAMPLE 2

Preliminary processing of kidney with diethylamine

Fifty (50) g of deep frozen, finely-divided grains of fresh calf kidney are to undergo chemical digestion (in the absence of oxygen and under the control of diethylamine) and are then to be dried.

The temperature of the frozen kidney substrate is $-180°$ C. The powder is placed in a thin layer on a petri dish and placed in a desiccator, in which a second vessel with 10 cc of diethylamine, and which is open, is placed. The diethylamine has a temperature of $0°$ C. On charging the apparatus the temperature of the kidney powder will go up to $-100°$ C. Using a powerful pump system a vacuum is produced in the desiccator as far as a value of 70 torr, because the vapor pressure of the diethylamine at $0°$ C. is 70 torr. Thereupon the connection with the pump system is shut off. By increasing the temperature of the diethylamine, this will undergo further evaporation. The gas undergoes reaction with the frozen kidney grains and is used up here. After the full amount of diethylamine has been evaporated on these lines, the connection with the vacuum pump is opened again and then using a cold trap, the substrate is dehydrated and the rest of the diethylamine is removed by exhaustion. Lastly, by connecting a diffusion pump directly to the apparatus, and not using (i.e. by-passing) the cold trap, the rest of the drying operation is undertaken.

EXAMPLE 3

Sterilization of infected chicken fetuses and egg membranes

This example is with respect to the inactivation of Newcastle disease virus (NDV) in chicken fetuses and egg membranes. The material is taken from infected, incubated hen's eggs and frozen in liquid nitrogen and pulverized. The frozen powder is placed in a thin layer on a petri dish and placed in a desiccator over a dish of concentrated sulfuric acid. The desiccator is joined up by way of a three-way valve with a high-vacuum pump and a pressure vessel in which there is 10 ml of a mixture of 97 parts of glacial acetic acid and 3 parts of 30% $H_2O_2$.

Firstly, the dessicator vessel is exhausted for 2 hours until the frozen powder has been dried to about one half to one quarter. Then, using the valve, the vacuum pump is shut off from the vessel and the further vessel with peracid mixture is connected to the desiccator so that the acid is evaporated and goes into the desiccator. The amount of acid evaporated will depend on the volume of the desiccator. In some cases, the vacuum in the desiccator vessel will have to be produced again and again to make certain that all the acid is evaporated. The time for taking effect is 30 minutes and thereafter exhaustion takes place until the powder is completely dry. However, even after the effect of the acid, the vessel with the acid may have its place taken by a vessel with mercaptoethanol, which is then caused to take effect on the tissue powder in the same way as was earlier the case with the acid, before the drying operation is stopped by undertaking exhaustion once again. Furthermore, in place of drying over hygroscopic concentrated sulfuric acid, freeze-drying using a cold trap may be used. The dried powder so produced will then be seen to be sterile on virological assay.

EXAMPLE 4

Sterilization of virus-infected dry powder

Virus-infected dry powder is placed in a 0.5 to 1 cm high layer in petri dishes, which are put in a desiccator. The desiccator is then evacuated. Water vapor is let into it and is condensed on the substrate so that the substrate is moistened. Evacuation is undertaken again. Then the vapors of an acid mixture made up of 1 part of performic acid and 2 parts of 98% of formic acid are let in. The further operations in this example are as those in Example 3.

EXAMPLE 5

Testing on animals

This example is with respect to the results of animal experiments, in which inbred mice, before transfer inocculation of $10^5$ tumor cells, were given three administrations of a suspension of 1 mg of dry powder of fetal bovine liver (which has been sterilized according to the procedure of Example 4) in physiological sodium chloride solution with 4 days between administration. The survival rate of the animals to which the dried powder was administered was 70%, while that of the control animals was 0%. The tests were undertaken with 10 inbred animals in each group, the reproducibility being made out to be less than or equal to ±5% using five test series.

In the therapeutic test, on the fifth, seventh and ninth days after administration of tumor material an additional 1 mg of dry powder of fetal bovine liver was injected as a suspension. In this case, survival rate was 80% of the animals and 0% in the case of the control animals.

EXAMPLE 6

Hemolysis plaque test

In the hemolysis plaque test, after pre-treatment with fetal bovine thymus preparations and in another case with fetal spleen, antibody synthesis was decreased below that in untreated animals in the test. Nine hundred thirty (930) antibody-forming spleen cells were found in the control animals in comparison with 875 in the case of the pre-treated animals.

EXAMPLE 7

Hemolysis plaque test

Using the hemolysis plaque technique, fetal cardiac muscle and furthermore brain was examined after two pre-treatments on the fourth and second days before administration of the antigen. In this respect, in the case of the untreated animals 378,000 plaque-forming cells were to be seen, while in the case of the treated animals the figure was 930,225 for each spleen. The highest value, which was produced with a bacterial toxin BA-1, was 690,000. In this case, 150 mg/kg bodyweight were administered once before antigen administration, while fetal heart at a dilution of 1 to 100, that is to say 10 mg, was injected on the fourth and second days before antigen administration.

EXAMPLE 8

Separation of ineffective components

One (1) g of the finely pulverized dry substance as produced in Example 1 from liver was homogenized in 100 ml of phosphate-buffered isotonic NaCl solution (pH 7.4) using a turbomixer at 6° to 10° C. and centrifuged at 200 g for 10 minutes. The supernatant top layer had the cytoplasmatic cell components, while the cell nucleus and membrane fraction was in the sediment. The sediment and the supernatant layers were separated and further processed.

(a) The supernatant layer was mixed with 40 ml of 5 mM tris-(hydroxymethyl)-aminomethane in 40mM NaCl with 10 ml of sodium taurocholate solution (80 mg/ml) and pH adjustment to 9.2 undertaken. After the addition of 2.5 ml of enzyme suspension (lipase) incubation was undertaken for two hours at 37° C. so that the lipids were degraded. For degradation of the polysaccharides to glucose, at a concentration of 10 mg of substrate/ml, pH value adjustment was undertaken with sodium acetate to 4.8. After the addition of amyloglucosidase, incubation was carried out for two hours at 40° C. Then the dialysis was undertaken against phosphate-buffered physiological NaCl solution (pH 7.4) for 24 hours or the substrate was ultrafiltered with a 600 molecular weight separation limit.

(b) For isolation of the DNA from the sediment, the last-named is suspended in 20 ml of 0.24M $Na_3PO_4$ (pH 6.8) with 1% SDS (sodium dodecylsulfate, 8M of urea and $10^{-3}$M EDTA (ethylenediaminetetraacetic acid) and this raw extract run into a 30 by 2.5 cm hydroxyapatite ($Ca_{10}(PO_4)_6(OH)_2$) column. RNA (ribonucleic acids), proteins and polysaccharides are eluated with 0.24M $Na_3PO_4$ (8M urea), while DNA is selectively produced in a second eluation step with 0.48M $Na_3PO_4$ buffer. cl EXAMPLE 9

(a) Coupling of DNA to the carrier material

An account will now be given of the coupling of DNA to cellulose used as the carrier substance for affinity-chromatography:

A DNA solution (1-2 mg/ml in 0.01M tris-(hydroxymethyl)-aminomethane-HCl, pH 7.4) with 0.001M EDTA is mixed with dry cellulose at a rate of 1 g of cellulose to 3 ml DNA solution. After overnight drying at room temperature the residual water is removed by freeze-drying, the power so produced is suspended in 20 parts by volume of tris-HCl and incubated for one day at 4° C. The excess DNA is removed by washing with buffer solution and the DNA-cellulose is diluted at a rate of 1 to 20 with buffer and placed in a 5 mm column.

(b) Coupling of proteins to carrier material.

The coupling of the proteins to agarose gel as the carrier material is undertaken after pre-treatment of the gel as will now be made clear:

Ten (10) g of the 2% gel are suspended in 5 ml of cold 5M $K_3PO_4$ buffer and the suspension diluted with distilled water to get an overall volume of 20 ml. BrCN (cyanogen bromide solution, 1 g/ml) is added in small amounts. The reaction time is 10 minutes. The product is washed until neutral on a glass sintered or fritted plate with $H_2O$. The proteins to be coupled (10–35 mg) in 0.25M $NaHCO_3$ solution at pH 9 with 2 g of the gel are placed in a reaction vessel. The coupling reaction comes to an end after 24 hours of rotation at room temperature. The products are placed in a small column and cleaned for 6 hours with 0.5M $NaHCO_3$, for 24 hours with 0.1M borate-0.1M NaCl (pH 8.5), for 12 hours with 0.1M Na acetate-1M NaCl (pH 4.1) and for 6 hours with double distilled water at a flow-through rate of 10 ml/hour. After this operation, it is possible for 120 micromole of glycine-leucine and 1.7 micromole/g of chymotrypsine to be coupled.

EXAMPLE 10

Selective adsorption and desorption of the active factor

The purpose of this example is to get the inhibiting and stimulating factor from the protein solution of juvenile bovine liver, which has been sterilized on the lines of the earlier examples and freed of ineffective components. For this purpose use is made of a rectangular gel apparatus for affinity-chromatography with electrodes at the outer long sides. The apparatus is filled with a DNA cellulose as produced in Example 9, the DNA having been produced from fetal bovine liver. The separating column is equilibrilized with 0.001M EDTA, 0.01M $Na_3PO_4$ (pH 7.4) at 37° C. The sample to be separated is dialyzed against the same buffer solution. It is then run into the separating apparatus at a concentration of 1 mg/ml, the primary eluate having the stimulating fraction in it. After a separating time of 8 hours, the apparatus was washed out with buffer solution. For secondary elution of the factors absorbed by the bound DNA, a further addition of buffer is made and the apparatus acted upon by an electric alternating field of 50 KHz at 1000 V, 5 mA. At the same time, the ionic strength of the buffer is continuously increased by the addition of NaCl up to 1M.

On using a direct current field (2000 V, 10 mA) separation in a way dependent on electrophoretic mobility may be produced at the same time, the substances being taken off from separate points. On using lower voltages and direct current, a different distribution, dependent on the current etc. of the primary eluate may be produced.

The fractions produced are assayed on cell cultures of diploid and heteroploid lines for measuring their efficacy. On doing this, the fraction with the most highly specific activity is made out, the charge then being standardized on this basis.

EXAMPLE 11

Producing tumor-inhibiting factors from a second eluate

For producing tumor-inhibiting factors from liver, the DNA fraction is isolated from a mixture of different solid tumors (for example melanoma, different sorts of carcinoma (breast, prostate, lung, stomach, intestine, brain) and possibly sarcomas from mesenchymal tissues together with the parallel metastases and leukemic cells, which have been bred in cultures (lymphatic cells and myeloic cells)). Then the factors are coupled as in Example 9 to cellulose and then as in Example 10 are used for separating or extracting a protein solution from liver. The inhibiting factor is produced by secondary elution and its specific inhibiting effect is tested on tumor cell cultures. On the same lines it is furthermore possible for DNA from single tumors and furthermore from fetal tissues, more specially, fetal placenta and liver, to be used. Furthermore, it is possible for body fluids to be separated on the same lines. Tumor-inhibiting fractions may be more specially produced from the maternal part of the placenta (decidua).

EXAMPLE 12

Producing stimulating active factors

Stimulating factors may be produced from liver or from the fetal part of the placenta (chorion) as a primary eluate by chromatography of the substrate on carrier-bound DNA from healthy tissues. The stimulating factors are produced or freed from the secondary eluate on using carrier-bound protein or peptide fractions for chromatography or other separating operations.

EXAMPLE 13

Producing organ-specific active factors

Organ-specific factors, for example from brain, may be produced using carrier-bound DNA or proteins from the organ in question, that is to say from the brain, on the same lines as the operation noted in Example 10. In the same sort of way age-specific, for example fetal stimulating factors may be produced on analogous carrier-bound DNA or protein fraction.

EXAMPLE 14

Inhibiting substances and stimulating factors taking effect on micro-organisms or plants, may be produced using carrier-bound DNA or proteins of the species in question.

EXAMPLE 15

Producing DNA fractions

The isolation of certain DNA's, which are effective as gene sections, may be undertaken from mixtures of DNA on protein fractions, isolated using the process of the present invention. Such substances will be seen to have a special effect on bio-assay testing. Such fractions may be used, when carrier-bound, for the affinity-chromatography of the parallel DNA mixtures or solutions, the DNA sections to be enriched or isolated being present in the secondary eluate.

EXAMPLE 16

Producing tumor-inhibiting factors (a) For producing tumor-inhibiting factors from fetal and juvenile calf liver, DNA from 100 g of meth-A-sarcoma tissue which was sterilized according to the present process was isolated on a chromatographic column according to the invention, which had been produced in animal experiments by implantation of tumor cells in inbred mice (see Example 26), the DNA being isolated using the process given in Example 22. Ten (10) mg of this tumor DNA were coupled to cellulose as in Example 23 and the DNA-cellulose, suspended in tris-EDTA-buffer, was placed in a 0.5×20 cm column. The column was used for separating 1 ml of the protein solution (purified as in Example 22) from juvenile or, in the other case, fetal calf liver with a protein or peptide level of 5 mg/ml. For this purpose, the column was eluated with a flow rate of 2 ml/hour using a tris-EDTA-buffer with an NaCl gradient of 0.1m to 2.0m. The fractions in the range running from 1.8m to 2.0m NaCl were collected and tested with respect to protein level and DNA level. The DNA polymerase-free fractions were dialysed against physiological saline or diafiltered using an ultracentrifuge (with a molecular weight of 600 for the limit of separation). Next, in animal experiments as in Example 26, the greatest tumor inhibition in the meth-A-sarcoma system was measured. In the case of three injections of 1 mg protein/animal on the +5th, +7th and +9th day after implantation of the tumor, the most strongly tumor-inhibiting fraction put up the survival rate to 80%–100% and the tumor regression to 60%–100% over the control. The unseparated raw extracts from calf liver were responsible, in the same test system, for survival rates of 40% to 70% and tumor regressions between 10% and 50%. The fraction giving the greatest inhibiting effect was tested in a number of different testing systems. By centrifuging at 300,000 g and by processing with proteinase the material was inactivated. Testing using PAA-electrophoresis gave at least 5 bands while SDS-electrophoresis, used as well, made it clear that there was a molecular weight scatter between about 600 and 1,000,000. More detailed identification of the active factors was not possible, even using the gel-chromatography, ion exchange chromatography, isoelectric focussing, preparative isotachophoresis and disk electrophoresis. All the non-biological ways of separating were responsible for decreased activity. For this reason, the active principle may be seen to be caused by a number of factors working together and which may only be enriched by DNA cellulose chromatography or other DNA affinity chromatographic processes. Furthermore, the purifying of these active factors may only be undertaken with these processes. The yield after purifying two times over was 10% (of the protein or peptide level of the raw extract) on using cellulose chromatography. The purified inhibiting fractions are buffer-soluble, undergo marked decomposition in a freeze-dried form at 50° C. upwards and are not degraded by DNA-ases and RNA-ases.

(b) For producing tumor-inhibiting factors from fetal or juvenile calf liver, the DNA from $3\times10^8$ human melanoma cells was isolated, which had been roller-cultured. The tumor DNA was coupled to cellulose as noted in part (a), the purified peptide or protein solution used in (a) being separated on the substrate. The DNA-polymerase-free fractions of the 1.8 to 2.0m NaCl eluate were tested as in Example 12 in the human cell culture on melanoma cells. The fraction with the greatest inhibiting effect reduced the DNA synthesis of melanoma cells within 8 hours in a concentration of $10^{-5}$ g/ml of culture medium to a level equal to only 10% of the control, whereas the unseparated raw extract gave, with the same peptide and protein concentration, an inhibition of the DNA biosynthesis to a level of 40% to 60% of the control.

(c) In place of the juvenile and fetal liver tissue preparations of decidua and thymus were prepared as noted in parts (a) and (b) and tested, the inhibition rates isolated as in (a) and (b) being of the same order.

EXAMPLE 17

Producing stimulating active factors

For producing stimulating active factors, the primary eluates of Example 1 (0.1m NaCl to 1.6m NaCl) were collected, the proteins and peptides being purified by diafiltration (with a 600 molecular weight separating limit) and coupled to agarose in the same way as detailed in Example 24. The protein-agarose conjugate was placed in an 1×60 cm column and a chorion extract, purified as in Example 22, was separated in the column using tris-HCl with a pH value of 7.4 (0.02m) as an elution buffer, the NaCl gradient being 0.01m to 4m. The fractions produced in the range 0.1m to 4m NaCl were tested with respect to their stimulation effect in human cell culture (see Example 27). The test cells being diploid fibroblasts which, by the addition of $10^{-5}$ g of protein/ml of culture medium of the strongest stimulation fraction, were stimulated by 160% to 210% (with respect to the control) in their DNA.

EXAMPLE 18

Pre-processing and sterilization with sulfuric acid in vacuo

One hundred (100) g of finely divided, virus-infected dry liver powder underwent distribution on a petri dish in a layer thickness of 0.5 cm and placed in a desiccator, the desiccator being connected, as desired, with a cryosorption condenser by way of a high vacuum pump system, and at the same time, however, with a vacuum vessel, which might be shut off from the main desiccator by a valve.

Firstly, concentrated sulfuric acid at room temperature was placed in the vacuum vessel and the valve (connecting to the desiccator) was turned off. To eliminate any moisture still present and caused by the hydroscopic effect of the dry powder, firstly, using the refrigerating condenser (which was supercooled with acetone-carbon dioxide snow) water was sublimed from the tissue powder and then, after turning off the condenser, evacuation was undertaken using a high vacuum plant until the pressure in the desiccator reached $10^{-4}$ torr, whereupon the value to the vacuum vessel was opened so that sulfuric acid vapor was able to make its way into the desiccator.

The vacuum level now became equal to the vapor pressure of sulfuric acid. Next, the connection with the acid vessel was shut off, but only after the vessel had been cut off from the pump plant. By blowing nitrogen into the desiccator, the vacuum over the liver powder was only decreased to a small degree further. For this reason, the sulfuric acid vapor was condensed onto the liver powder. After a certain time for it to take effect, the connection between the pump system and the vessel for the acid was opened up again and, after getting to the vapor pressure of sulfuric acid, the operation was undertaken two further times. At the end, the connection between the desiccator and the pump system was opened up again, but not between the two vessels. Pumping then took place until all sulfuric acid had been cleared from the desiccator which had not taken part in a chemical reaction. In this way, the hydrogen ion concentration in the dry liver powder may be made more or less acid as desired. The longer and the stronger the evacuation, the more neutral the pH value.

On using preparations infected with New Castle disease virus (NDV) it was possible to see that the virus had been completely inactivated. Furthermore, test micro-organisms (E. coli) were completely inactivated by this processing.

EXAMPLE 19

Pre-processing and sterilization with diethylamine

Fifty (50) g of deep-frozen, finely divided particles of fresh calf kidney were to be digested chemically in the absence of oxygen and with control by diethylamine, and then dried. The temperature of the deep-frozen kidney substrate was −180° C. After distribution of the powder in a thin layer on a petri dish, the dish was placed in a desiccator together with a second vessel with 10 cc of diethylamine, the two vessels being kept open. The diethylamine had a temperature of 0° C. By the time the kidney powder has been placed in the desiccator its temperature had increased to −100° C. The desiccator was then evacuated by a powerful pump system to achieve a vacuum of 70 torr, this being the vapor pressure of diethylamine at 0° C. Then the desiccator was shut off from the pump system and by increasing the temperature of the diethylamine, the same was further evaporated, the gas undergoing reaction with the frozen kidney particles and being used up by them. After all the diethylamine has been evaporated in this way, the connection with the vacuum pump was opened again and firstly using a cryosorption unit, the substrate was dehydrated, the rest of the diethylamine being taken off by evacuation. At the end, by connecting to a diffusion pump and bypassing the cryosorption unit, the rest of the drying operation was undertaken.

EXAMPLE 20

Pre-processing and sterilization with peracids

This example is with respect to the inactivation of New Castle disease virus (NDV) in hen egg fetuses and oval membranes, which, after being taken from infected, brooded hens' eggs were deep-frozen in liquid nitrogen and finely divided. After distribution of the deep-frozen powder in a thin layer on a petri dish, it was placed in a desiccator over a dish full of concentrated sulfuric acid, the desiccator being connected by means of a three-way cock with a high vacuum pump and a pressure vessel having in it 10 ml of a mixture of 97 parts of glacial acetic acid and 3 parts of 30% $H_2O_2$.

Firstly, evacuation of the desiccator vessel took place for two hours until the frozen powder had dried to about ½ to ¼ and then the vacuum pump was shut off from the vessel by way of the valve and the vessel or receptacle with the peracid mixture was opened so that the receptacle was connected to with the desiccator and the acid evaporated, the acid making its way into the desiccator. The amount of acid evaporating was dependent on the volume of the desiccator. If necessary, the vacuum in the desiccator vessel had to be produced twice over so that all the acid was evaporated, the time for taking effect amounting to 30 minutes. After this, evacuation took place until the powder was completely dry. However, it was furthermore possible, after the acid had taken effect, for the receptacle for the acid to have its place taken by a receptacle with mercaptoethanol which was then, on the same lines as was the case with the acid earlier, caused to have its effect on the tissue powder before the drying operation was ended by evacuating again. Furthermore, in place of drying over the hydroscopic, concentrated acid, freeze-drying using a cryosorption trap was possible. The dried powder produced was seen to be sterile on virological examination.

EXAMPLE 21

Pre-processing and sterilization with peracids

Virus (NDV)-infected dry powder was placed in a layer with a thickness of 0.5 cm to 1 cm on petri dishes which were placed in a desiccator which was then evacuated and then water vapor was let into it, the vapor condensing on the substrate and moistening it. Then evacuation was undertaken again, the vapors being forced into an acid mixture made up of 1 part of performic acid and 2 parts of 98% formic acid. In other respects, the operation was as in Example 20.

EXAMPLE 22

Clearing inactive components according to step (b)

One (1) g of the finely divided dry liver substance produced in Example 18 was homogenized in 100 ml of phosphate-buffered isotonic NaCl (pH 7.4) by a turbomixer at 6° C. to 10° C. and centrifuged at 200 g for 10 minutes, the cytoplasmatic cell components being in the supernatant liquid whereas the cell nucleus and membrane fraction were in the sediment, the sediment and supernatant liquid being separated for further processing.

(a) The supernatant liquid was mixed with 40 ml of 5mM of tris(hydroxymethyl)-aminomethane in 40 mM NaCl with 10 ml sodium taurocholate solution (80 mg/ml) and pH adjustment to 9.2 undertaken and after the addition of 2.5 ml of enzyme suspension (lipase) incubation was undertaken for two hours at 37° C. for degrading the lipids.

For degrading the polysaccharides to glucose, a concentration of 10 mg of substrate/ml was used, pH adjustment to 4.8 being undertaken with sodium acetate. After the addition of amyloglucosidase, incubation took place for two hours at 40° C. whereafter the material was dialysed for 24 hours against phosphate-buffered physiological NaCl (pH 7.4) or the substrate was ultrafiltered with a separating limit at a molecular weight of 600.

(b) For isolating the DNA, the same was taken up in 20 ml of 0.24M $Na_3PO_4$ (pH 6.8) with 1% SDS (sodium dodecyl sulfate), 8M urea and $10^{-3}$M EDTA (ethylenediaminetetraacetic acid) as a suspension, whereupon this raw extract was put in a 30×2.5 cm hydroxyapatite ($Ca_{10}(PO_4)_6(OH)_2$) column. RNA (ribonucleic acids), proteins and polysaccharides were eluted with 0.24M $Na_3PO_4$ (8M urea), while DNA was obtained selectively in a second eluate with 0.48M $Na_3PO_4$ buffer.

EXAMPLE 23

Coupling of DNA to cellulose as a carrier substance for affinity chromatography according to step (c)

A DNA solution (1-2 mg/ml in 0.01M tris-(hydroxymethyl)-aminoethane-HCL (pH 7.4) with 0.001M EDTA was mixed with dry cellulose at a rate of 1 g of cellulose to 3 ml of DNA solution. After drying overnight at room temperature, the rest of the water was taken off by freeze-drying and the powder so produced was taken up on 20 parts by volume of tris HCL and incubated for one day at 4° C. Uncoupled DNA was cleared by washing with buffer solution and the DNA-cellulose was diluted with buffer at a rate of 1:20 and filled into a 5 mm column.

EXAMPLE 24

Coupling of proteins to agarose gel as a carrier substance after pre-processing of the gel Ten (10) g of the 2% gel were taken up in 5 ml of cold 5M $K_3PO_4$ buffer and the suspension produced diluted with distilled water to an overall volume of 20 ml. BrCN (cyanogen bromide solution) 1 g/ml was added in small amounts. After a reaction time of 10 minutes, the product was washed until neutral on a glass frit using $H_2O$. The proteins (10 mg to 35 mg) to be coupled in 0.25M $NaHCO_3$ solution at pH 9 were placed with 2 g of the gel in a reaction vessel, the coupling reaction coming to an end after 24 hours of turning the vessel at room temperature. The products were purified in a small column for 6 hours using 0.5M $NaHCO_3$, for 24 hours using 0.1M borate-0.1M borate-0.1M NaCl (pH 8.5), for 12 hours with 0.1M sodium acetate-1M NaCl (pH 4.1) and 6 hours with doubly distilled water with a current or flow rate of 10 ml/hour. After this part of the process it was possible for 120 micromoles of glycine-leucine and 1.7 micromoles/g of chymotrypsin to be coupled.

EXAMPLE 25

Selective adsorption and desorption of the active factors according to step (d)

The inhibiting and stimulating factors were separated from a protein solution from juvenile bovine liver, which as in the earlier examples, was sterilized and freed from undesired components. Use was made, for this purpose, of a rectangular flat gel apparatus for affinity chromatography with electrodes on the outer long sides.

The apparatus was charged with DNA-cellulose produced as in Example 9, the DNA having been produced from fetal bovine liver. The separating column was equilibrated with 0.001M EDTA, 0.01M $Na_3PO_4$ (pH 7.4) at 37° C. The sample to be separated was dialysed against the same buffer solution. It was then placed in a concentration of 1 mg of protein/ml into the separating apparatus. The primary eluate had within it the stimulating fraction. After a separating time of 8 hours, the apparatus was washed through with buffer solution. For secondary elution of the factors absorbed by the coupled DNA, on making a further addition of the buffer, an electric alternating current field of 50 KHz and 1000 V. 5 mA was caused to take effect. At the same time the ionic strength of the buffer was steplessly increased by the addition of NaCl up to 1M.

On using a direct current field (2000 V. 10 mA) it is possible for separation to take place in a way dependent on the electrophoretic mobility for output at separate points. By using lower voltages and direct current, a representative distribution of the primary eluate may be caused.

The fractions produced were tested on cell cultures of diploid and heteroploid cell lines for activity assay to make out the fraction with the highest specific activity, this then being used for standardizing the charge.

EXAMPLE 26

Activity assay of active factors obtained according to the present invention in animal experiments The experimental animals were (Balb/c-x C57/b16) $F_1$ mice (from Jackson Laboratories, Bar Harbour, Maine, USA).

The tumor system used was meth-A-sarcoma. The tumor cells were passaged weekly by the parenteral injection of $1 \times 10^6$ cells. On the 7th to 12th days after the parenteral injection the cells were used for the experiments.

For the tests $1 \times 10^5$ tumor cells were injected intracutaneously onto the skin of the belly. Exponential tumor growth then took place which, after about 4 to 5 weeks, was responsible for the death of the animals. The experiments were undertaken with 10 animals in each group. The treatment of the verum groups took place by one to three intramuscular or intravenous injections each 1 mg (measured as protein) of the test fractions.

EXAMPLE 27

Activity assay of active factors obtained according to the present invention in human cell culture Human tumor cells (melanoma, Wish) and diploid fibroblasts (F.H.2, MRC-5) were used as test cells, all cell cultures going through a test cycle which was made up of two growth phases and a minimum phase, addition of the test substances taking place in the minimum phase.

Growth phase 1: The cells, which had been stored under liquid nitrogen, were suddenly thawed and incubated together with MEM-II-medium (Instamed, Seromed, Munich) with additions of penicillin, streptomycin, neomycin and 10% of fetal calf serum at 37° C. After two days the cells were optically counted after trypsinizing, the cells then being sown again ($2 \times 10^6$ cells in each bottle).

Growth phase 2: After daily change of medium on the 4th day the cells were counted again and groups of $0.5 \times 10^6$ cells were each sown in small culture bottles, together with nutrient medium and serum addition.

Minimum phase: After 24 hours the medium was cleared off by aspiration and a minimum medium with a decreased serum addition (diploid cells: 1%, heteroploid cells: 0.25%) was put in.

Test phase: After 48 hours addition of the preparation took place, 50 microliters of preparation being put in each bottle in the present tests. For each sort of preparation and concentration 3 parallel samples were made up. In the case of short time tests action was limited to 8 hours. Four hours before the end of this time in each case 50 microliters of methyl-$^3$H-thymidine solution (0.5 micro Ci) were put in with a pipette. At the end of the action time, the thymidine which had not been built in, was cleared by washing four times with 4 separate amounts of 5 ml of 2% perchloric acid and the cells were hydrolysed for one hour using 1N HCL at 70° C. The hydrolysate was placed in scintillation flasks and mixed with cocktail (aquasol 2, NEN). Activity was measured in a Beckman LS-100 Liquid Scintillation Counter. As statistical quality numbers, relative stand and deviations of the overall test system of $s_r \pm 10\%$ were achieved.

EXAMPLE 28

Active factors obtained in according to the present invention for plants

For producing syntheses-stimulating and, on the other hand, growth-inhibiting materials taking effect on grasses and cereals, 10 kg of roots and leaves of a mixture of different sorts of plants was processed with a 0.1% NaOCl or $O_3$ disinfectant solution for taking effect on micro-organisms, the solution taking effect on the outer faces of the plant material being put in by dipping or spraying. After this, the disinfectant solution was completely cleared by washing and the pieces of plant material were externally dried generally completely, cut up in a rasp mill and then, once this had been done, pressed at +5° C. to 10° C. in a plant press at up to 200 atmospheres gage. The fresh expressed juice was freed by centrifuging at 800 rpm to 1000 rpm for 3 minutes, or in a continuous flow centrifuge, of corpuscular components and then filtered sterile, whereupon adjustment of the molecular weight to a value greater than 1 million took place. The filtrate was frozen in liquid nitrogen and freeze-dried in a high vacuum at room temperature. The dried material was finely divided and sulphatized by being acted upon by vapor or concentrated sulfuric acid or phosphatized by being acted upon by vapors of concentrated phosphoric acid (85%). The dry powder was now dissolved in isotonic aqueous NaCl mixed with carbohydrate-(or starch)-degrading, or furthermore, lipid-degrading enzymes coupled to a carrier substance. Such carrier coupled enzymes may be cleared by centrifuging, after degrading the substrates, and used again. The low molecular weight substances produced on degrading up to a molecular weight of 600 were cleared by filtering. Proteins and nucleic acids were cleared from fractions with a higher molecular weight using known methods. One part of the expressed juice processed on these lines was used for producing nucleic acids by degrading the protein components using proteolytic enzymes (papain or trypsin) and the nucleic acids (DNA and RNA) chemically coupled with a carrier substance was then placed in a chromatographic column and the other part of the expressed juice separated thereon. In the primary eluate (0.1M NaCl) growth-stimulating factors were present. By using an increasing ionic strength (2M NaCl) proteins absorbed thereon or peptides, were eluated, these being the growth-inhibiting active factors.

The isolated active factors were tested on cultured (see Example 12) protoblasts or plant embryoes to see their effect on the synthesis metabolism of DNA, RNA or protein by using radioactive base compounds as for example $^3H$-thymidine or $^3H$-uridine or, with respect to the cell proliferation, by optical counting. Inhibition produced by the isolated factors was greater than 5% of the controls while stimulation was greater than 10% in a minimum medium.

EXAMPLE 29

Active Factors for micro-organisms obtained in accordance with the present invention In races of yeast, which had good alcohol fermentation properties, the fermentation property was further activated and the resistance to alcohol increased so that on fermentation higher alcohol concentrations might be produced. For this purpose, nucleic acids and proteins were separated from the yeast races in question, mixed with other sorts of yeasts as in Example 22. Separation was undertaken on the same lines as in the case of organic substances (Example 18) by sudden freeze-drying of the washed yeasts, finely dividing and drying in a frozen condition and suspending or dissolving in isotonic physiological solvent.

After this, the separating material was produced from isolated nucleic acids, which were covalently coupled to a carrier substance, which was then charged into the separating apparatus (on the same lines as in Example 23). It was then possible for nucleic acids, carbohydrates and lipids to be enzymatically degraded by carrier-coupled enzymes from the protein solution to be separated, the enzymes being separated at the end of the reactions, by centrifuging.

It was, however, possible for the raw extract as well to be separated in a separating apparatus. In the primary eluate the stimulating factors were present while the secondary eluate coming from the separating material had the inhibiting factors. Then the stimulating factors were added to the yeast suspension, to be used for producing alcohol, in a concentration of milligrams to nanograms/g or ml. In this respect the yeasts were suspended in a physiological solution without nutrients or a minimum nutrient solution. After causing the stimulating factor to take effect on the yeast suspension for one hour at 20° C., addition to the malt to be fermented was undertaken.

On the same general lines, other active factors may be produced for the use against other micro-organisms as for example oil-degrading microbes. The inhibiting biological active factors may furthermore be used therapeutically as biological antibiotics.

EXAMPLE 30

Active factors obtained in accordance with the present invention for use against viruses Inhibiting factors for use against viruses were produced by separating nucleic acids (DNA or RNA) and proteins or peptides from isolated viruses or virus-infected tissues, as for example egg membranes, the nucleic acids being used as separating materials (see furthermore Examples 16 to 27). These inhibiting factors were produced from the protein solution, produced at the same time, or furthermore from tissue extracts produced from healthy and, as far as possible, virus-resistant cells from individuals or cell cultures. The virus-inhibiting factors were present in the secondary eluate (1.8M to 2M NaCl).

I claim:

1. A process for the concentration of biologically active factors having an inhibiting effect on the growth of neoplastic cells from cell homogenates of fetal or juvenile tissues or body fluids which contain said biologically active factors, which comprises the steps of:
   (a) non-destructively sterilizing said cell homogenates with an acid or diethylamine;
   (b) separating the components of cell nucleus and cytoplasmic components from the sterilized starting material;
   (c) enzymatically decomposing lipids and carbohydrates which are obtained from step (b) with an enzyme selected from the group consisting of lipase, proteinase and peptidase;
   (d) separating the cell substrate and recovering a factor having a molecular weight from about 600 to about 1,000,000;

(e) forming a conjugate with DNA isolated from a cell homogenate with an inert carrier and forming a biologically active affinity sorbent means responsive to selective separation with said conjugate;
(f) selectively separating said biologically active factors by elution on said affinity sorbent, and then
(g) separating said biologically active factors from said affinity sorbent by electrophoresis or by a buffer solution, whereby an enriched amount of said biologically active factors is recovered.

2. The process of claim 1 wherein the cell substrate to be separated and the biologically active affinity sorbent are each prepared from like organs, species or age-specific tissue.

3. The process of claim 1 wherein said cell substrate is fetal thymus or fetal pancreas tissue.

4. The process of claim 1 wherein said cell substrate is finely divided and sterilized by a vacuo condensation of vapors of a member selected from the groups consisting of concentrated sulfuric acid, acetic acid, formic acid, diethylamine and peracids.

* * * * *